(12) United States Patent
Lichtenstein et al.

(10) Patent No.: US 8,377,075 B2
(45) Date of Patent: Feb. 19, 2013

(54) SYSTEM AND METHODS FOR CLEARANCE OF OBSTRUCTIONS

(76) Inventors: Steven Lichtenstein, Merion Station, PA (US); David W. D'Angelo, Broomall, PA (US)

( * ) Notice: Subject to any disclaimer, the term of this patent is extended or adjusted under 35 U.S.C. 154(b) by 513 days.

(21) Appl. No.: 11/897,259

(22) Filed: Aug. 28, 2007

(65) Prior Publication Data

US 2008/0287734 A1 Nov. 20, 2008

Related U.S. Application Data

(63) Continuation-in-part of application No. 11/731,725, filed on Mar. 30, 2007, now abandoned.

(51) Int. Cl.
*A61D 1/12* (2006.01)
(52) U.S. Cl. ........................................................ 606/106
(58) Field of Classification Search .................. 606/106; 66/113; 433/91
See application file for complete search history.

(56) References Cited

U.S. PATENT DOCUMENTS

| | | | | |
|---|---|---|---|---|
| 4,445,509 A * | 5/1984 | Auth | ............................. | 606/159 |
| 4,657,016 A * | 4/1987 | Garito et al. | .................... | 606/45 |
| 5,871,481 A * | 2/1999 | Kannenberg et al. | ........... | 606/34 |
| 6,090,103 A * | 7/2000 | Hakky et al. | .................... | 606/14 |
| 6,299,839 B1 * | 10/2001 | Karunaratne et al. | .......... | 422/63 |
| 6,939,359 B2 * | 9/2005 | Tu et al. | ........................ | 606/159 |
| 6,971,988 B2 * | 12/2005 | Orban, III | ..................... | 600/104 |
| 2004/0087988 A1 | 5/2004 | Heitzmann et al. | | |
| 2005/0182438 A1 | 8/2005 | Scopton et al. | | |
| 2005/0234493 A1 | 10/2005 | Carr et al. | | |

* cited by examiner

*Primary Examiner* — Gary Jackson
*Assistant Examiner* — Christopher Schubert
(74) *Attorney, Agent, or Firm* — Valauskas Corder LLC

(57) ABSTRACT

The present invention is a system and methods to clear obstructions including foreign objects and food boluses during an EGD procedure. The medical device according to the present invention includes a flexible tubular housing, power transfer device, clamp, tool element, power source, and optional hood. The present invention drills through the obstruction to rupture it into pieces. Displaced obstructions, and/or pieces thereof, can be collected within the housing. The remainder of the obstruction can then be passed into the stomach where it can be digested, safely excreted, or actively removed by an endoscopist.

2 Claims, 3 Drawing Sheets

SYSTEM AND METHODS FOR CLEARANCE OF OBSTRUCTIONS

This application is a continuation in part of U.S. patent application Ser. No. 11/731,725 filed Mar. 30, 2007 now abandoned.

FIELD OF THE INVENTION

The present invention generally relates to a medical system and methods and, more particularly, to a system and methods to clear obstructions within the upper gastrointestinal tract.

BACKGROUND OF THE INVENTION

Foreign object ingestion and food bolus impactions are a common occurrence. Urgent intervention is required to prevent aspiration and perforation. Foreign object ingestion or food bolus impaction creates an obstruction. Obstruction is anything that is obstructs, blocks, or closes off a bodily cavity. Food bolus impactions occur in the upper gastrointestinal tract (GI tract), with the most common site of impaction at the stomach-esophagus (gastro-esophageal) junction, or at other regions of narrowing within the esophagus. The upper GI tract consists of the mouth, pharynx, esophagus, stomach and duodenum terminating at the ligament of Treitz.

Typically, an initial endoscopic examination verifies, locates and identifies the obstruction. An endoscope is shaped as a long tube, which is inserted through the mouth into the esophagus and stomach to identify the foreign object or food bolus. Once the foreign object or food bolus has been identified with the endoscope, various instruments can be passed through the endoscope to grasp and remove or displace the obstruction. An endoscopist is a person trained to use an endoscope.

The foreign object or food bolus can usually be removed en bloc or in a piecemeal fashion with the instruments. Instruments include forceps, which come in varying shapes, sizes and grips, snares, and oval loops that can be retracted from outside the endoscope to lasso objects, as well as baskets, or mesh nets that can be closed to trap small objects, and magnets placed at the end of the scope. Some techniques have been described that use catheters to trap objects, or use two snares to orient foreign bodies.

These current instruments are not ideal in that they each are limited to specific uses. Furthermore, a "pull" and "push" technique is required. This technique requires the instrument to be manipulated by pulling it back and then pushing it gently to displace the obstruction into the stomach. This is not desirable for objects that cannot be digested or that cannot be safely excreted. Nor is this technique desirable to perform on obstructions that are firmly impacted with the upper GI tract including the walls of the esophagus.

As an alternative to the endoscopic clearance described, a food bolus impaction can be cleared passively through the use of medication, such as Glucagon. This approach is often not successful.

The currently available instruments for foreign object ingestion and food impaction clearance are not ideal. Likewise, medication does not offer consistent success to passively clearing a food impaction. Thus, there is a strong need for improvement in the clearance of obstructions in the upper gastrointestinal tract.

SUMMARY OF THE INVENTION

The present invention clears obstructions including foreign objects and food boluses by drilling through the obstruction to rupture or displace the obstruction in order to clear it. The obstruction is cleared by passing into the stomach where it can be digested or safely excreted. The obstruction can also be cleared by actively removing it from the human cavity by an endoscopist. The present invention is applicable to anything that can be swallowed and subsequently obstructs the upper GI tract.

The present invention includes a flexible tubular housing, such as a catheter device. The flexible tubular housing can further include one or more retainers therein. The retainers can be any size or shape that allows displaced obstructions, and/or pieces thereof, to be collected, for example, pockets, chambers, or compartments. The housing can be inserted into a human cavity, typically via an endoscope. The housing can be any material that is flexible, for example metal or plastic such as stainless steel, aluminum, titanium, silicone, or polyurethane. Although the tubular housing is flexible, it must maintain a tensile strength to stabilize the other components of the medical device, such as the clamp and tool element, throughout the procedure.

A power transfer device, for example drive shaft, catheter or laser, is positioned within the tubular housing, extending therethrough. The power transfer device may rotate as well as vacillate, or move in and out of the housing. It is also contemplated certain embodiments of the present invention do not include a power transfer device such that the housing itself rotates as well as vacillates, or move in and out of the human cavity. In one embodiment, a drive shaft power transfer device includes a clamp that is rotated by a power source that provides electrical output, mechanical or manual output, or power. The power transfer device and clamp can be any material for example metal or plastic such as stainless steel, aluminum, titanium, silicone, or polyurethane. It is further contemplated the power transfer device, or the housing itself, can function as a retainer to collect displaced obstructions. A laser power transfer device includes a coherent beam of light.

The output from the power source can be automatic, manual, and even computer controlled. The power source can further include a regulator for adjusting the power, for example by a knob or foot pedal. Likewise, the output applied to the power transfer device can be variable or fixed. Output is in the form of rotational speed, or revolutions per minute (rpm). Examples of power sources include electrical power supplies, mechanical or manual power supplies, linear power supplies and computer power supplies.

The clamp securely holds removable parts and includes a receiving unit to accept tool elements. Clamps can include collets and chucks such as pin chuck, drill chuck, magnetic chuck, three or more-jaw chuck, snap-fit configuration to name a few. It is also contemplated that the clamp is universal such that it receives all shaped and sized tool elements.

A tool element is received within the receiving unit of the clamp. Tool elements come in a variety of shapes and sizes such that the appropriate tool element is used for the procedure. It is contemplated that the tool elements may be disposable or re-used upon sterilization.

Tool elements include bits. Bits are cutting tools to create cylindrical-shaped holes, although bits are also available for non-cylindrical-shaped holes. Bits can be of any material that displaces and clears the obstruction, for example metal such as stainless carbide steel or carbine tungsten steel. Bits include a cutter and a shank. Shanks are received within the receiving unit of the clamp. Shanks include brace shanks, straight shanks, hex shanks, SDS shanks, triangle shanks, and morse taper shanks, for example. Different styles of shank/clamp combinations deliver different performance, such as allowing higher torque or greater centering accuracy.

Tool elements may also include lasers that vaporize, or burn, the obstruction. The laser can be a solid state laser such as yttrium aluminum garnet (YAG) or any other type including gas lasers, chemical lasers and excimer lasers.

Tool elements also include a hole saw, or hole saw-type device, which may be manufactured from plastic or steel. A hole saw-type device uses teeth to displace and clear the obstruction.

The present invention may further include a hood, such as a shield, guidepost, or guard. The hood surrounds the tool element to protect the human cavity and walls of the cavity from injury. The hood can be of any flexible material, for example metal or plastic such as stainless steel, aluminum, titanium, silicone, or polyurethane.

It is an object of the present to provide a system and method that can be mechanical-based, water-based, cautery-based, or laser-based. A mechanical-based system and method utilizes machine parts, whereas a water-based system and method utilizes a device to deliver water to the obstruction during the procedure. A cautery-based system and method utilizes a caustic device, such as a hot iron, electric current, or fire to burn the obstruction. A laser-based system and method utilizes a coherent beam of light to clear the obstruction.

It is an object of the present invention to provide a system and method that provides a rapid and safe removal of an obstruction from the upper GI tract of a patient.

Another object of the present invention is to improve patient safety. The present invention decreases the amount of anesthetic needed for anesthetic as well as decreases the risk for damaging the upper GI tract during the procedure.

An object of the present invention is to reduce the time it takes to clear an obstruction.

The present invention and its attributes and advantages will be further understood and appreciated with reference to the detailed description below of presently contemplated embodiments, taken in conjunction with the accompanying drawings.

DETAILED DESCRIPTION OF EMBODIMENTS OF THE INVENTION

The present invention is applicable to anything that can be swallowed and subsequently obstructs the upper GI tract. The present invention clears obstructions, including foreign objects and food boluses, to be passed into the stomach for digestion or safe excretion or actively removed from the human cavity by an endoscopist.

Figure 1:
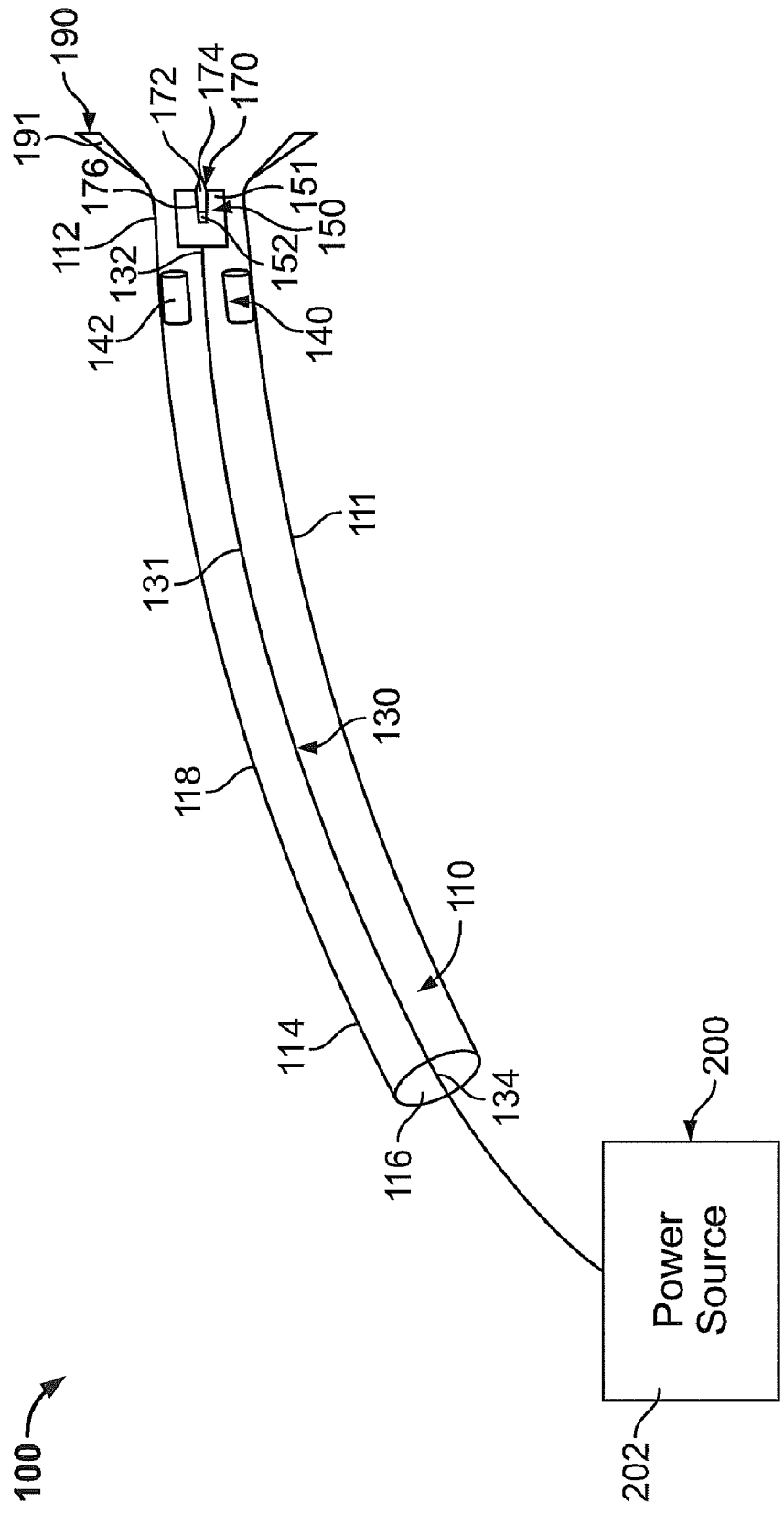
FIG. 1 illustrates a perspective view of the medical device according to the present invention.
Figure 2:
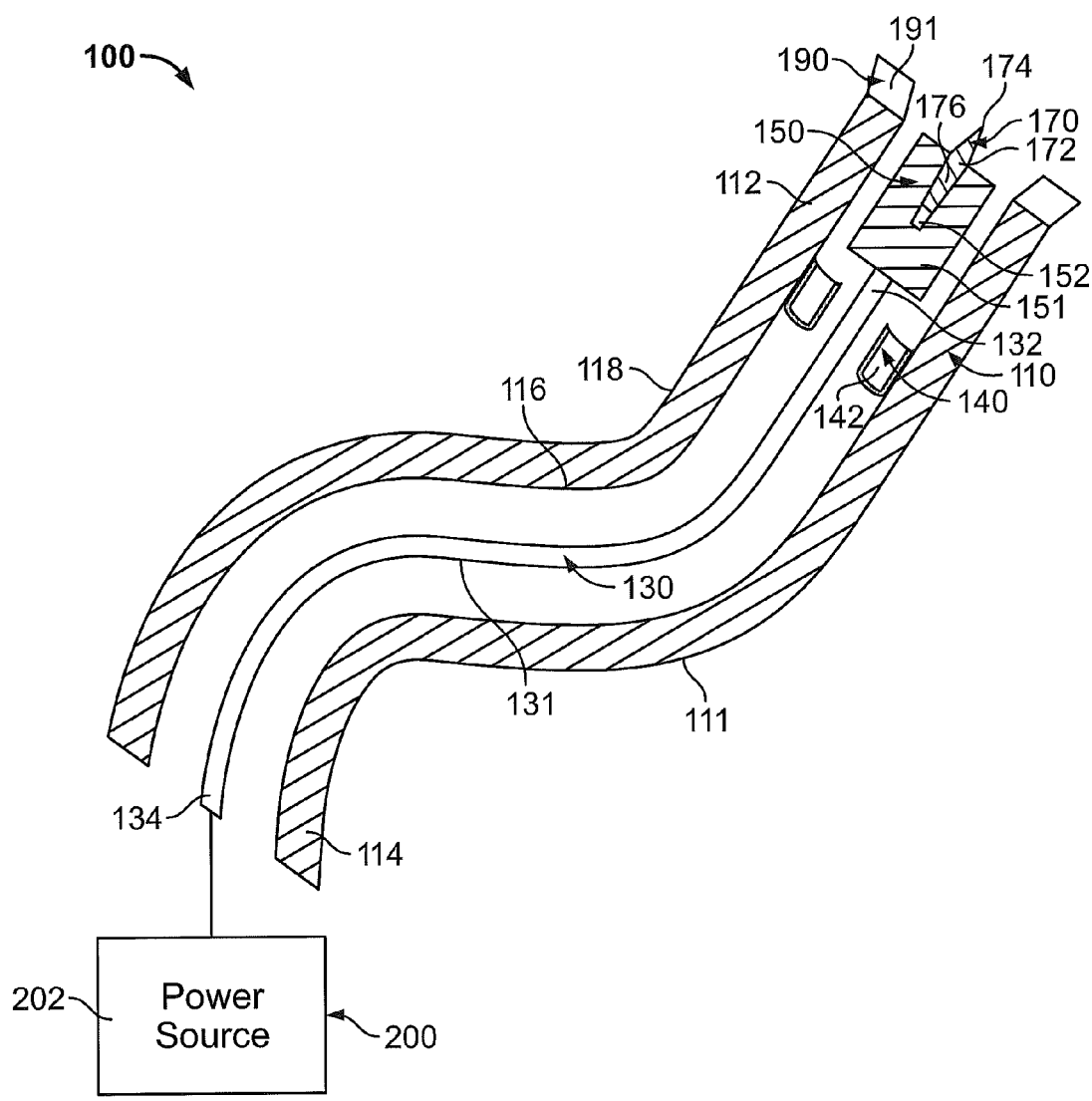
FIG. 2 illustrates a cross-sectional side view of the medical device according to the present invention.

As shown in FIGS. 1 and 2 the mechanical-based medical device 100 according to the present invention includes a flexible tubular housing 110, power transfer device 130, clamp 150, tool element 170, hood 190 and power source 200.

The housing 110 includes a distal end 112 and proximal end 114. The housing 110 includes an inner diameter 116 and outer diameter 118 extending from the distal end 112 to the proximal end 114. Housing 110 further includes one or more retainers 140 positioned within the inner diameter 116 of the housing 110. Retainers 140 collect displaced obstructions, and/or pieces thereof, for removal.

A power transfer device 130 includes a first end 132 and a second end 134 with a clamp 150 positioned at the first end 132. Clamp 150 includes a receiving unit 152 to receive tool elements 170. Hood 190 surrounds the tool element 170 to protect the human cavity from injury during the procedure.

As shown more specifically in FIGS. 1 and 2, housing 110 is a catheter 111 and power transfer device 130 is a drive shaft 131. Catheter 111 includes retainers 140 that are cylindrical columns 142. Drive shaft 131 is positioned within inner diameter 116 of catheter 111. Clamp 150, here a chuck 151, is positioned at the first end 132 of drive shaft 131. Upon positioning drive shaft 131 within inner diameter 116, chuck 151 is positioned at distal end 112 of catheter 111. Chuck 151 includes a receiving unit 152 for engagement with a tool element 170, here a bit 172. Bit 172 includes a cutter 174 and a shank 176. Shank 176 is received within receiving unit 152.

An electrical power supply 202 is connected to the drive shaft 131 for rotation of the chuck 151. Guidepost 191 protects the body cavity and walls of the body cavity from injury during the procedure.

Once a patient has been diagnosed with a foreign object ingestion and/or food bolus impaction, the patient is prepared for an esophago-gastro-duodenoscopy (EGD) procedure.

An endoscope is inserted into the esophagus to verify, locate and identify the obstruction. The end of the endoscope is placed at the obstruction and the medical device 100 according to the present invention is then passed through the endoscope. Thus, the distal end 112 of the catheter 111 is positioned at the obstruction.

Upon reaching the obstruction, the medical device 100 is powered by an electrical power supply 202 to rotate the drive shaft 131 and chuck 151. Consequently, the bit 172 positioned with the chuck 151 rotates to drill through the obstruction causing it to rupture into pieces. Likewise, displaced obstructions, and/or pieces thereof, can be collected into the cylindrical columns 142 within the flexible catheter 111. The medical device 100 can further include a guidepost 191 to protect the esophagus from injury, for example, caused by inadvertent misdirection of the bit 172. The pieces of the obstruction are then passed into the stomach where the obstruction can be digested, safely excreted, or actively removed by an endoscopist.

Figure 3:
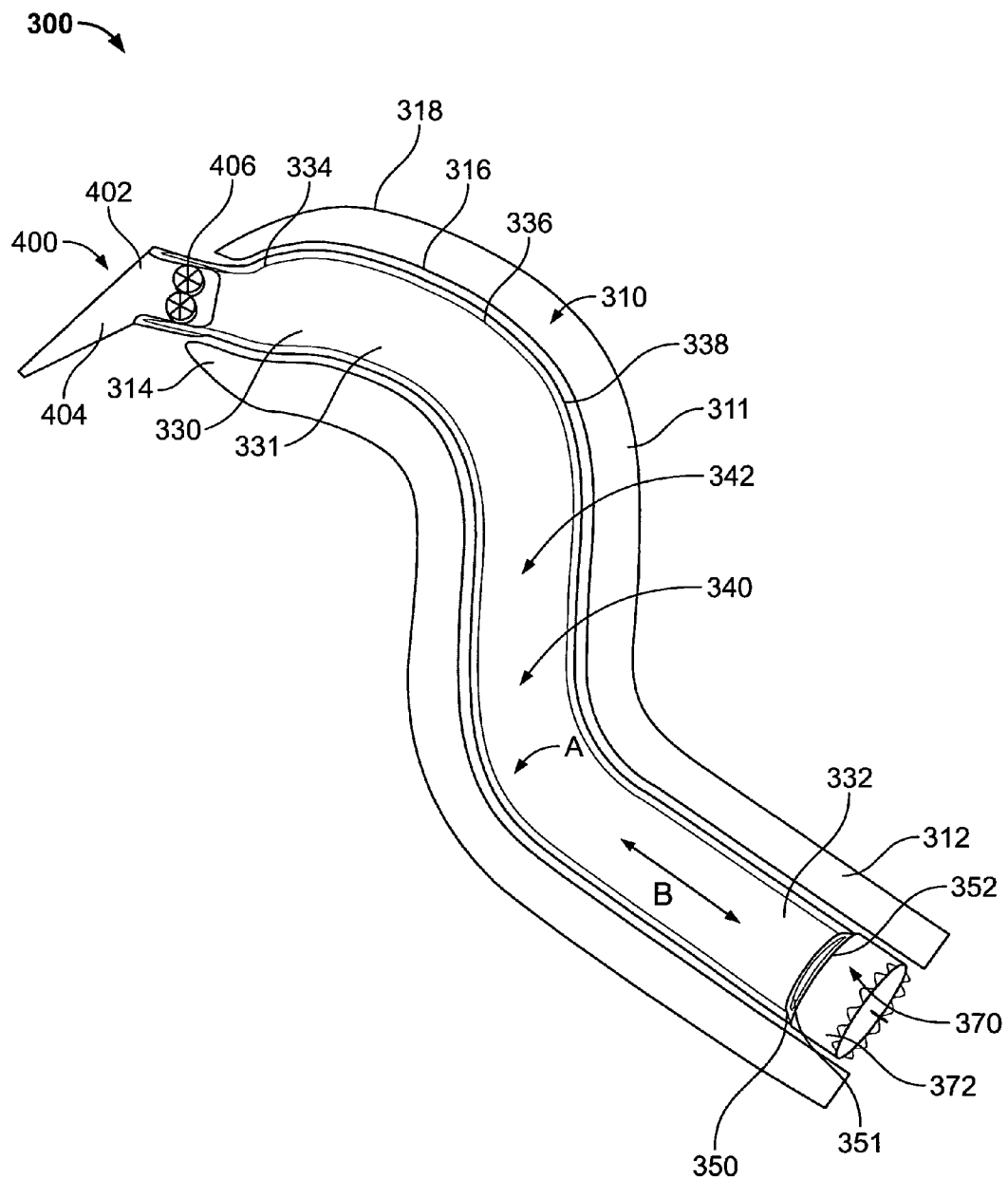
FIG. 3 illustrates a cross-sectional side view of an alternate embodiment of the medical device according to the present invention.

A medical device 300 utilizing a mechanical power supply 400 is shown more specifically in FIG. 3. As shown in FIG. 3, the mechanical-based medical device 300 according to the present invention includes a flexible tubular housing 310, power transfer device 330, clamp 350, tool element 370, and mechanical power source 400. It is contemplated the medical device 300 may further include a hood (not shown) to protect the human cavity from injury during the procedure.

The housing 310 includes a distal end 312 and proximal end 314. The housing 310 includes an inner diameter 316 and outer diameter 318 extending from the distal end 312 to the proximal end 314.

A power transfer device 330, here a catheter 331, includes a first end 332 and a second end 334 with a clamp 350 positioned at the first end 332. Clamp 350 includes a receiving unit 352 to receive tool element 370. It is also contemplated certain embodiments of the present invention do not include a power transfer device 330 such that the housing 310 includes a clamp 350 with a receiving unit 352 to receive a tool element 370.

The catheter 331 further includes an inside diameter 336 and an outside diameter 338. The space 342 defined by the inside diameter 336 of the catheter 331 acts as retainer 340 positioned therein. Retainers 340 collect displaced obstructions, and/or pieces thereof, for removal.

The mechanical power supply 402 is connected to catheter 331. Although it is also contemplated the catheter 331 can be connected to an electrical power supply or a computer power supply. The mechanical power supply 402 is operated by manual hand crank 404, but is also contemplated to be any structure, for example a rotating lever, to manually rotate the catheter 331 including tool element 370. In certain embodiments of the present invention that do not include a power transfer device 330, housing 310 includes a clamp 350 with a tool element 370 wherein the housing 310 may rotate as well as move in and out of the human cavity.

In one embodiment, the manual hand crank 404 includes a gear reduction system 406 to allow slow calculated rotations of the tool element 370.

As shown in FIG. 3, housing 310 is a flexible plastic tube 311 that includes a catheter 331. Upon positioning catheter 331 within inner diameter 316 of the tube 311, clamp 350 is positioned at distal end 312 of the tube 311 as well as at the first end 332 of the catheter 331. In one embodiment, clamp 350 is a snap-fit configuration which includes a receiving unit 352 for engagement with a tool element 370, here a hole saw-type device 372.

After diagnosis, the patient is prepared for an esophago-gastro-duodenoscopy (EGD) procedure. Subsequent to insertion of an endoscope into the esophagus, the medical device 300 is passed through the endoscope.

Thus, the distal end 312 of the tube 311 is positioned such that the hole saw-type device 372 is at the obstruction. Upon reaching the obstruction, the medical device 300 is powered by manipulating the hand crank 404 to rotate the catheter 331 including hole saw 372. The catheter 331 can be manipulated to rotate as shown by arrow A in FIG. 3, as well as vacillate, or move in and out of the housing as shown by arrow B. Consequently, the hole saw 372 rotates to drill through the obstruction causing it to rupture into pieces.

Likewise, displaced obstructions, and/or pieces thereof, can be collected into space 342 defined by the inside diameter 336 of the catheter 331. The pieces of the obstruction are then passed into the stomach where the obstruction can be digested, safely excreted, or actively removed by an endoscopist.

While the disclosure is susceptible to various modifications and alternative forms, specific exemplary embodiments thereof have been shown by way of example in the drawings and have herein been described in detail. It should be understood, however, that there is no intent to limit the disclosure to the particular embodiments disclosed, but on the contrary, the intention is to cover all modifications, equivalents, and alternatives falling within the scope of the disclosure as defined by the appended claims.

What is claimed is:

1. A medical device, comprising,
    a flexible tubular housing sized and shaped to be positionable within an upper gastrointestinal tract space, said flexible tubular housing including an inner diameter and an outer diameter extending from a distal end to a proximal end;
    a catheter positioned within said inner diameter of said flexible tubular housing including a first end and a second end and an inside diameter and an outside diameter;
    a clamp including a receiving unit positioned at said first end of said catheter;
    a tool element fully engaged within said receiving unit of said clamp; and
    a power supply positioned at said second end of said catheter, wherein said power supply moves said catheter including said clamp and said tool element to engage a foreign obstruction within the upper gastrointestinal tract space thereby rupturing the foreign obstruction into pieces,
    wherein at least one retainer is fixedly positioned within said catheter and collects the pieces of the foreign obstruction.

2. The medical device of claim 1 further comprising a hood at said distal end of said flexible tubular housing, wherein said hood surrounds said tool element to protect portions of the upper gastrointestinal tract space.

* * * * *